United States Patent [19]

Coats

[11] Patent Number: 4,594,360
[45] Date of Patent: Jun. 10, 1986

[54] CHLORONITROALKANE INSECTICIDES

[75] Inventor: Joel R. Coats, Ames, Iowa

[73] Assignee: Iowa State University Research Foundation & Inc., Ames, Iowa

[21] Appl. No.: 674,493

[22] Filed: Nov. 23, 1984

[51] Int. Cl.$^4$ ................. A01N 33/20; A01N 33/22; C07C 79/35
[52] U.S. Cl. .................. 514/716; 568/585; 568/586
[58] Field of Search ................ 568/585, 586; 514/716

[56] References Cited

U.S. PATENT DOCUMENTS

| | | | |
|---|---|---|---|
| 3,657,357 | 4/1972 | Holan | 568/586 |
| 3,823,192 | 7/1974 | Holan | 568/586 |
| 3,995,063 | 11/1976 | Strong et al. | 568/585 X |
| 4,004,023 | 1/1977 | Strong et al. | 568/585 X |

OTHER PUBLICATIONS

Hass et al., *Industrial and Eng. Chem.*, vol. 43, (1951), 2875–2888.

Primary Examiner—Bernard Helfin
Attorney, Agent, or Firm—Zarley, McKee, Thomte, Voorhees & Sease

[57] ABSTRACT

Compounds of the formula

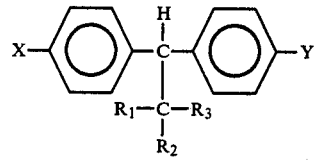

wherein X is a $C_1$ to $C_3$ alkoxy group, Y is selected from the group consisting of halogens, $C_1$ to $C_4$ alkyl, and $C_1$ to $C_3$ alkoxy, and $R_1$, $R_2$ and $R_3$ are selected from the group of chloro, nitro and hydrogen, with at least one of $R_1$, $R_2$ and $R_3$ being chloro, and at least one of $R_1$, $R_2$ and $R_3$ being nitro, are useful in combatting insects.

14 Claims, No Drawings

CHLORONITROALKANE INSECTICIDES

BACKGROUND OF THE DISCLOSURE

The substituted diphenylalkanes have progressed through several stages of evolution over the past 45 years. The first commercially successful example in this class was DDT. Different types of stuctural modifications have resulted in many other series of insecticidal compounds, including a number of other commercial products. Each series of new derivatives developed has also contributed to a greater data base from which structure-activity relationships can be drawn. Steric effects such as size, position, branching, and symmetry among substituents have been demonstrated to be important to the biological activity. Electronic factors, e.g., electronegativity, also exert effects at the site of action, the nerve axon. Lipophilicity is also a parameter that contributes to toxicity of the diphenyl alkanes.

There is obviously a continuing and primary need for new insecticidal compositions widely effective against pests and insects when applied in economically feasible quantities.

Accordingly, this invention has as its primary objective, the development of new insecticides using many of the valuable properties of diphenylalkane insecticides of the past, but still having other certain structural moiety modifications which are designed to make the new derivatives more highly effective from the standpoint of their steric effects upon biological activity, and their electronic factors which affect actions at the site of the nerve axon and finally, which affect their lipophilicity, all designed to significantly enhance the toxicity of the diphenylalkane.

It is another primary objective of the present invention to provide certain diphenylalkane insecticides which can be easily synthesized, which are easy to work with, which have a kill efficiency that is considered good at relatively low levels of usage, and which have an overall significantly improved utility for general insecticidal uses.

SUMMARY OF THE INVENTION

Certain para, para' disubstituted diphenyl halonitroalkanes have been found to be insecticides of wide-ranging activity that have: (1) excellent activity against a broad spectrum of insects, (2) good residual activity, and (3) good mammalian safety ratios. The compounds and their use in insecticidal compositions are both parts of this invention.

DETAILED DESCRIPTION OF THE INVENTION

This invention relates to para, para' disubstituted diphenyl halonitroalkanes. In particular, the compounds are 1,1-diphenyl-2-chloro-2-nitroethanes and/or 1,1 diphenyl-2,2-dichloro-2-nitroethanes of the formula:

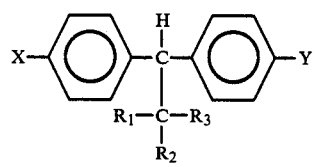

wherein X is a $C_1$ to $C_3$ alkoxy group, Y is selected from the group consisting of halogens, $C_1$ to $C_4$ alkyl, and $C_1$ to $C_3$ alkoxy, and $R_1$, $R_2$ and $R_3$ are selected from the group of chloro, nitro and hydrogen, with at least one of $R_1$, $R_2$ and $R_3$ being chloro, and at least one of $R_1$, $R_2$ and $R_3$ being nitro.

Structure-activity studies have indicated that X and Y groups of proper size and shape with appropriate groups of $R_1$, $R_2$ and $R_3$ act as good insecticides. Most certainly steric factors account for some of the optimal potency of these compounds; however, they alone are not totally the reason for activity. Specific toxicological studies on insect nerve indicate that increasing electronegativity in the aliphatic moiety may enhance insecticidal activity, see Brown, et al., Structure-Activity Relationships of DDT-Type Analogs Based on the In Vivo Toxicity to the Sensory Nerves of the Cockroach, Periplaneta americana, J. Pestic. Biochem. Physiol. 15:43-57 (1981). Put another way, electron donating substituents (at least one) on the rings, it is believed may also provide for greater insecticidal potency. Thus, the analogs of the present invention have at least one electron donating group present on the ring.

X in the above described formula represents a $C_1$ to $C_3$ alkoxy group, that is methoxy, ethoxy or propoxy. Y is selected from the group consisting of halogens, preferably chlorine, $C_1$ to $C_4$ alkyl and $C_1$ to $C_3$ alkoxy. One of either X or Y has to be an alkoxy group. The limits for the alkoxy group of $C_1$ to $C_3$ are present because beyond $C_3$ the moiety becomes too bulky such that it will not fit the receptor in the insect's nerve. The halogen for Y can be chloro, bromo or fluoro or ioodo, but is preferably chloro. The alkyl group of $C_1$ to $C_4$ may be straight or branched chain, and for example, tertiary butyl will work as well. The reasons for the limits of $C_1$ to $C_3$ for the alkoxy are the same as the reason for the limit on the X group. Ethoxy is the preferred alkoxy group. Y may also be haloalkyls, such as trifluoromethyl.

All of the Y substituents may be classified as lipophilic in character and non-polar groups. It is essential that they be lipophilic and non-polar, because polar groups will not penetrate the insect cuticle, while lipophilic groups aid in permeability, and in addition, the size restrictions and the effect on the stability of the compound will be impaired if others are employed. Thus, the ones mentioned have been found most desirable from the standpoint of insecticidal activity and stability.

$R_1$, $R_2$ and $R_3$ are selected from the group consisting of chloro, hydrogen and nitro, with at least one of $R_1$, $R_2$ and $R_3$ being chloro, and at least one of the others being nitro. Again, the reason for this is that enhanced biological activity has been found to be the result of the greater electron withdrawing groups that are on the side chain of the diphenylalkane. Put another way, the more electron withdrawing the groups, such as chloro and nitro, the better the action of the compound on the insect nervous system to provide neurotoxic action. Chloro and nitro are good electron withdrawing groups, and also provide a molecule of stability, ease in preparation and having other desirable processing and handling characteristics.

Thus, although the active compounds are useful per se in combatting insect pests, it is preferable in practicing the method of the present invention, that the active compounds be applied to the pests or to the environment of the pests in a dispersed form in a suitable carrier agent. In this specification the term "dispersed" is used in its widest possible sense, thus, the term means that particles of the active compounds may be molecular in size and held in true solution in a suitable organic solvent; the term also means that the particles may be colloidal in size and distributed throughout a liquid phase in the form of suspensions or emulsions or in the form of particles held in suspension by surface-active agents of a non-ionizing character; the term also means that the particles can be distributed in a semi-solid viscous carrier such as petroleum or other ointment base of a non-ionizing character in which they may be actually dissolved in the semi-solid or held in suspension in the semisolid with the aid of suitable non-ionizing surface-active agents; the term also means that the particles may be mixed with and distributed throughout a solid carrier providing a mixture in particulate form, e.g., pellets, granules, powders or dusts; and the term also means that the particles can be in mixtures which are suitable for use as aerosols including solutions, suspensions or emulsions of the active compounds in a carrier such as dichlorodifluoromethane and like fluorochloroalkanes or mixtures of these and/or with other substances which boil below room temperature at atmospheric pressure. In this specification and appended claims, the expression "insecticidal carrier" includes any and all of those substances in which the active compounds are disbursed, including therefore, the solvents of a true solution, the liquid phase of suspensions, emulsions or aerosols, the semi-solid carrier of ointments, and the solid phase of particulate solids, e.g., pellets, granules, dusts and powders.

The concentration of the active compounds employed according to the invention in combatting insect pests can vary considerably provided the required dosage (i.e., toxic or lethal amount) thereof is supplied to the pests or to the environment of the pests. When the carrier agent is a liquid or mixture of liquids as in solutions, suspensions, emulsions or aerosols, the concentration of the active compound employed to supply the desired dosage generally will be in the range of 0.001 percent to 50 percent by weight. When the carrier agent is a semi-solid or solid, the concentration of the active compounds employed to supply the desired dosage generally will be in the range of 0.01 percent to 25 percent by weight.

There are a large number of organic liquids which can be used for the preparation of solutions, suspensions or emulsions of the active compounds. For example, isopropyl ether, acetone, methyl ethyl ketone, octanone, dioxane, cyclohexanone, carbon tetrachloride, ethylene dichloride, tetrachloroethane, hexane, heptane, and like higher liquid alkanes, hydrogenated naphthalenes, solvent naphtha, benzene, toluene, xylene, petroleum fractions (e.g., those boiling almost entirely under 400° F., and having a flash point above about 80° F., particularly kerosene), mineral oils having an unsulfonatable residue above about 80 percent and preferably above about 90 percent. In those instances wherein there may be concern about the phytotoxicity of the organic liquid extending agent, a portion of the same can be replaced by such low molecular weight aliphatic hydrocarbons as dipentene, diisobutylene, propylene trimer, and the like or suitable polar organic liquids such as the aliphatic ethers and the aliphatic ketones containing not more than about 10 carbon atoms as exemplified by acetone, methyl ethyl ketone, diisobutyl ketone, dioxane, isopropyl ether, and the like. In certain instances, it is advantageous to employ a mixture of organic liquids as the carrier agent, e.g., an aromatic hydrocarbon and an aliphatic ketone.

When the active compounds are to be supplied to the insect pests or to the environment of the pests as aerosols, it is convenient to dissolve said compounds in a suitable solvent and disperse the resulting solution in dichlorodifluoromethane or chlorofluoroalkane or mixtures of these or with other aerosol dispersants which boil below room temperature at atmospheric pressure. In this connection the invention provides as a new article of manufacture, suitable for combatting flying insects, particularly DDT resistant mosquitoes, in and around the household, an aerosol pressure-pack containing a pressurized container enclosing an aerosol composition embodying said active compounds.

The active compounds are preferably applied to the insect pests or to the environment of the insect pests in the form of emulsions or suspensions. Emulsions or suspensions are prepared by dispersing the active compounds either per se or in the form of an organic solution thereof in water with the aid of a water-soluble non-ionic surfactant. The term "surfactant" as employed in this specification is used as in Volume II of Schwartz, Perry and Berch's "Surface Active Agent and Detergents" (1958), Interscience Publishers, Inc., New York) in place of the expression "emulsifying agent", to connote generically the various "emulsifying agents", "dispersing agents", "wetting agents", and "spreading agents" that are adapted to be admixed with the active compounds in order to secure better wetting and spreading of the active compounds in the water vehicle or carrier in which the active compounds are insoluble through lowering the surface tension of the water (see also Frear "Chemistry of Insecticides, Fungicides, and Herbicides", second edition, page 280). The surfactants contemplated are the well-known capillary active substances which are non-ionizing (or non-ionic) and which are described in detail in Volumes I and II and Schwartz, Perry and Berch's "Surface Active Agent and Detergents" (1958, Interscience Publishers, Inc., New York) and also in the November 1947 issue of *Chemical Industries* (pages 811–824) in an article entitled "Synthetic Detergents" by John W. McCutcheon and also in the July, August, September and October 1952 issues of Soap and Sanitary Chemicals under the title "Synthetic Detergents". The disclosures of these articles with respect to non-ionizing capillary active substances are incorporated in this specification by reference in order to avoid unnecessary enlargement of this specification. The preferred surfactants are the water-soluble non-ionic surface-active agents.

The active compounds can be dispersed by suitable procedures (e.g., tumbling or grinding) in solid carrier agents either of organic or inorganic nature and applied to the insect pests environment in particulate form. Such solid materials include for example, tricalcium phosphate, calcium carbonate, kaolin, bole, kieselguhr, talc, bentonite, charcoal, fuller's earth, pyrophillite, diatomaceous earth, calcined magnesia, volcanic ash, sulfur and the like inorganic solid materials, and include for example, such materials of organic nature as powdered cork, powdered wood, and powdered walnut shells. The preferred solid carriers are the adsorbent clays, e.g., bentonite. These mixtures can be used for insecticidal purposes in the dry form, or by addition of water-soluble, non-ionic surfactants, the dry particulate solids can be rendered wettable by water so as to obtain stable aqueous dispersions or suspensions suitable for use as sprays. For special purposes the active compounds can be dispersed in a semi-solid carrier agent such as petrolatum with or without the aid of solubility promoters and/or non-ionic surfactants.

A concentrate, for example in the form of a spray base or particulate solid base, may be provided in such form that by merely mixing with water or with a solid carrier (e.g., powdered clay or talc) or other low-cost readily-available material, an easily prepared spray or particulate solid isecticide for household or agriculture purpose can be produced. In such a concentrate composition the above active compounds generally will be present in a concentration of 5 to 95 percent by weight, the residue being any one or more of the well-known insecticidal adjuvants, such as the surface-active clays, solvents, diluents, carrier media, adhesives, spreading agents, humectants, and the like.

The synthetic pathway to the compounds of this invention can be illustrated as shown in equations 1 and 2 below.

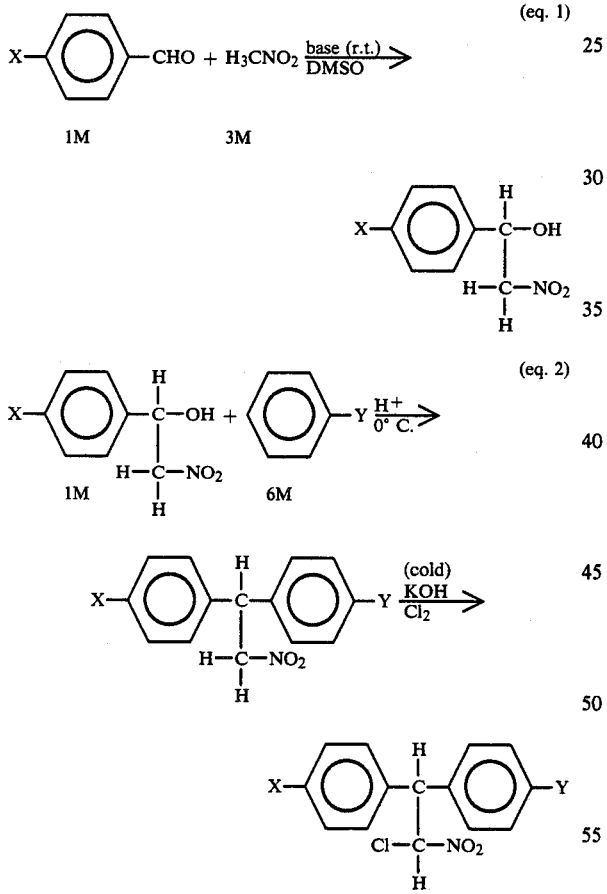

The base used in tests so far was DBN or 1,5-diazabicyclonon-5-ene. Numerous other bases have been utilized and could be utilized as well, such as sodium methoxide, sodium bicarbonate, triethylamine, potassium hydroxide and pyridine. Carbinol intermediates represented as the product of equation 1 need not be purified prior to use in the condensation reaction. DMSO of course, in equation 1, represents dimethyl sulfoxide.

In the second equation, the acid used is a mixture of concentrated sulfuric and glacial acetic acids.

Alternative methods of synthesis to that outlined above are, of course, chlorination of the carbinol intermediate followed by condensation with a substituted benzene or chlorination of nitromethane followed by reaction with a substituted benzaldehyde and then a substituted benzene. Preliminary testing on the compounds has indicated effectiveness against mosquito larvae and house flies.

EXAMPLES

Insecticidal activity of the new compounds of the formula presented herein were demonstrated in tests against mosquito larvae. The compound was made in accordance with the synthetic pathway illustrated in equations 1 and 2, wherein both X is ethoxy and Y is chloro, $R_1$ and $R_2$ were chloro, and $R_3$ was nitro. The compound was confirmed by nuclear magnetic resonance and samples were tested on mosquito larvae, utilizing a standard World Health Organization test method. In particular, 100 milliliters of water were placed in several cups, along with ten mosquito larvae of the species Culex pipiens were placed in each cup. The active insecticide as explained above was placed in a one milliliter volume of acetone and added to each cup and the mortality of the mosquitoe larvae were recorded for a 24-hour period. The concentration of the active range from 0.1 part per billion to ten parts per million and the data is summarized in the following table.

TABLE 1

Toxicity of p-ethoxyphenyl-1-p-chlorophenyl-2,2-dichloro-2-nitroethane to mosquito larvae (4th instar) Culex pipiens. Mortality at different doses expressed as μg of insecticide per ml of water, or parts per million (PPM) recorded 24 hours after treatment. Ten larvae were used for each container of 100 ml of water.

| Treatment | Number dead/Number exposed | % Mortality |
|---|---|---|
| none (control) | 0/10 | 0 |
| acetone (control) | 3/30 | 10 |
| 10 ppm | 20/20 | 100 |
| 1 ppm | 20/20 | 100 |
| .5 ppm | 20/20 | 100 |
| .1 ppm | 39/40 | 98 |
| .01 ppm | 20/20 | 100 |
| .005 ppm | 20/20 | 83 |
| .001 ppm | 19/20 | 95 |
| .0005 ppm | 5/20 | 25 |
| .0001 ppm | 10/20 | 50 |

$LC_{50}$ = 0.00058 ppm
95% confidence intervals
lower = 0.00047
upper = 0.00071

What is claimed is:

1. Compounds of the formula:

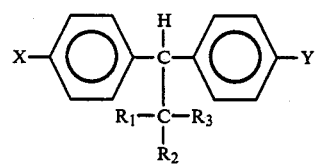

wherein X is a $C_1$ to $C_3$ alkoxy group, Y is selected from the group consisting of halogens, $C_1$ to $C_4$ alkyl, and $C_1$ to $C_3$ alkoxy, and $R_1$, $R_2$ and $R_3$ are selected from the group of cloro, nitro and hydrogen, with at least one of $R_1$, $R_2$ and $R_3$ being chloro, and at least one of $R_1$, $R_2$ and $R_3$ being nitro.

2. A compound of claim 1 wherein X and Y are both alkoxy.

3. A compound of claim 2 wherein X and Y are both ethoxy.

4. A compound of claim 1 wherein $R_1$ is nitro, $R_2$ is hydrogen and $R_3$ chloro.

5. An insecticidal composition comprising as an essential active ingredient, an insecticidal amount of compound of the general formula:

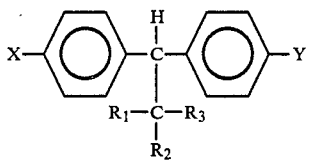

wherein X is a $C_1$ to $C_3$ alkoxy group, Y is selected from the group consisting of halogens, $C_1$ to $C_4$ alkyl, and $C_1$ to $C_3$ alkoxy, and $R_1$, $R_2$ and $R_3$ are selected from the group of cloro, nitro and hydrogen, with at least one of $R_1$, $R_2$ and $R_3$ being chloro, and at least one of $R_1$, $R_2$ and $R_3$ being nitro and an inert insecticidal carrier for said compounds.

6. A compound of claim 5 wherein X and Y are both alkoxy.

7. A compound of claim 5 wherein X and Y are both ethoxy.

8. A compound of claim 5 wherein $R_1$ is nitro, $R_2$ hydrogen, and $R_3$ chloro.

9. A composition of claim 5 wherein the concentration of active is from 5% to 95%, with the balance being an insecticidal adjuvant.

10. The composition of claim 9 wherein said adjuvant is petrolatum in combination with a solubility promoter and a non-ionic surfactant.

11. A method of devitalizing insects, comprising the step of subjecting them to the action of an insecticidal amount of a compound of the general formula:

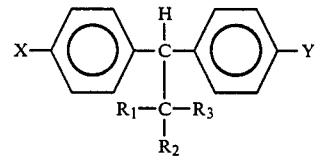

wherein X is a $C_1$ to $C_3$ alkoxy group, Y is selected from the group consisting of halogens, $C_1$ to $C_4$ alkyl, and $C_1$ to $C_3$ alkoxy, and $R_1$, $R_2$ and $R_3$ are selected from the group of cloro, nitro and hydrogen, with at least one of $R_1$, $R_2$ and $R_3$ being chloro, and at least one of $R_1$, $R_2$ and $R_3$ being nitro.

12. A compound of claim 11 wherein X and Y are both alkoxy.

13. A compound of claim 11 wherein X and Y are both ethoxy.

14. A compound of claim 11 wherein $R_1$ is nitro, $R_2$ hydrogen, and $R_3$ chloro.

* * * * *